US00PP37386P3

(12) United States Plant Patent
Bennett

(10) Patent No.: US PP37,386 P3
(45) Date of Patent: Apr. 28, 2026

(54) SHRUB ROSE PLANT NAMED 'AUSB44A16'

(50) Latin Name: *Rosa hybrida*
Varietal Denomination: AUSB44A16

(71) Applicant: DAVID AUSTIN ROSES LIMITED, Albrighton (GB)

(72) Inventor: Carl Bennett, Albrighton (GB)

(73) Assignee: David Austin Roses Limited, Albrighton (GB)

( * ) Notice: Subject to any disclaimer, the term of this patent is extended or adjusted under 35 U.S.C. 154(b) by 0 days.

(21) Appl. No.: 18/980,052

(22) Filed: Dec. 13, 2024

(65) Prior Publication Data

US 2026/0090485 P1 Mar. 26, 2026

(30) Foreign Application Priority Data

Sep. 24, 2024 (QZ) ..... PBR 20242225

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
CPC ..... A01H 5/0222
See application file for complete search history.

(56) References Cited

U.S. PATENT DOCUMENTS

PP23,099 P3 10/2012 Austin

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of shrub rose plant, referred to by its cultivar name, 'AUSB44A16', is described. The new variety forms pink-blend, mid-pink colored blossoms. The flowers have approximately 120-130 petals. The new variety provides a shrub growth habit. Additionally, the new variety is particularly well suited for growing as ornamentation in the landscape.

2 Drawing Sheets

CROSS REFERENCE TO RELATED APPLICATIONS

Figure 1:
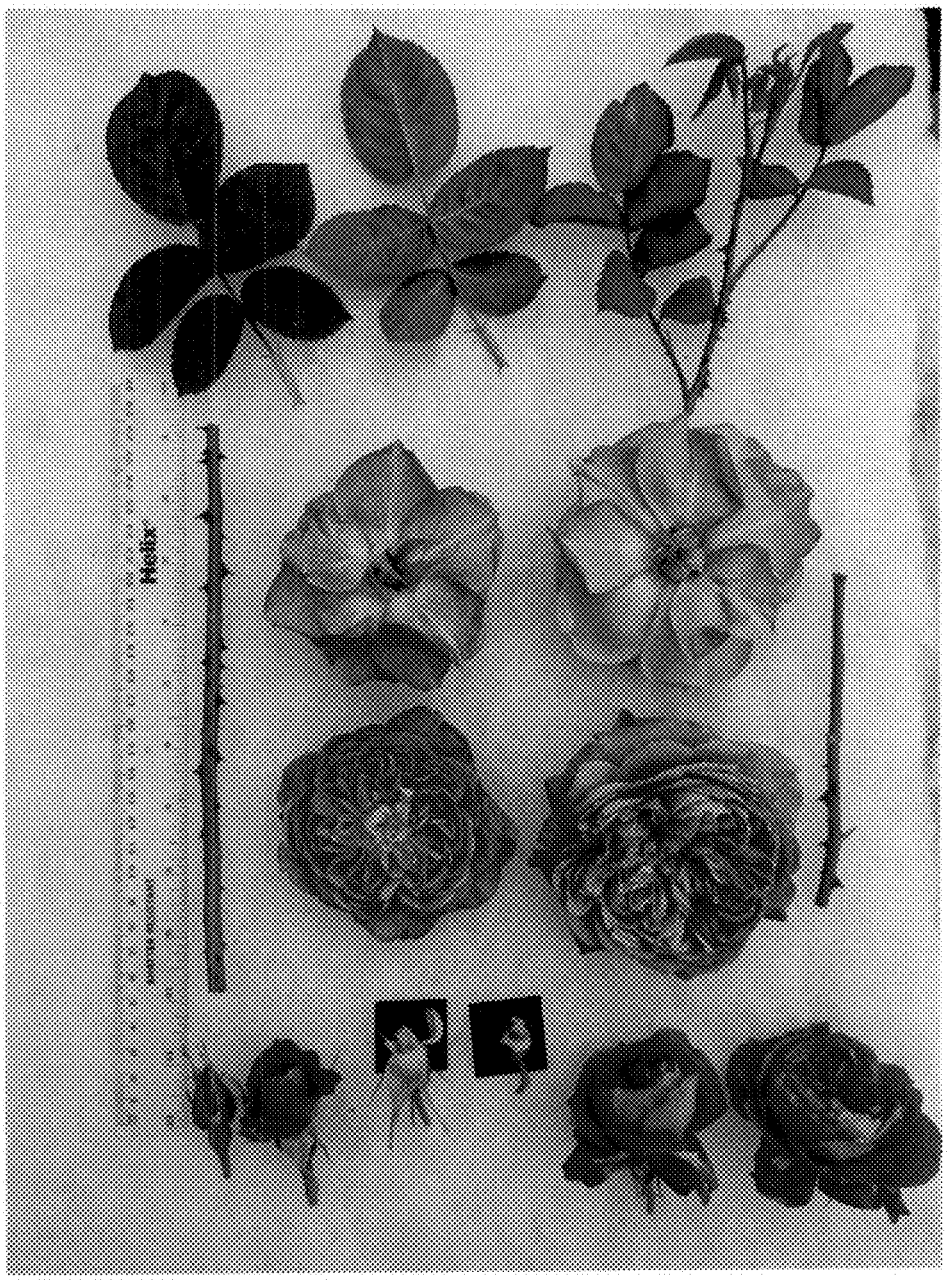

This application claims priority to Plant Breeders' Right Application No. 20242225, which was filed at Community Plant Variety Office in the European Union on Sep. 24, 2024, the contents of which are hereby incorporated by reference for all purposes.

Latin name of genus and species of plant claimed: *Rosa hybrida.*

Variety denomination: 'AUSB44A16'.

STATEMENT REGARDING PRIOR DISCLOSURES BY THE INVENTOR

The first sale and offer for sale of the new variety was May 20, 2024, in the United Kingdom at a trade show. The first offer for sale and first sale of the new variety, and subsequent offer for sales and sales, was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of shrub rose plant of the present invention was created by controlled breeding during 2013, in Albrighton, England by artificial pollination wherein two parents were crossed which previously had been studied in the hope that they would contribute the desired characteristics. The female parent (i.e., the seed parent) of the new variety an unnamed seedling (not patented). The male parent (i.e., the pollen parent) of the new variety was a different unnamed seedling (not patented).

The parentage of the new variety can be summarized as follows:

Unnamed seedling x Different unnamed seedling

The seeds resulting from the above pollination were sown in January 2014, and small plants were obtained which were physically and biologically different from each other. Selective study resulted in the identification of a single plant of the new variety in July 2014. Eight buds from the selected single plant of the new variety were taken and grafted, using the T-budding method, onto Rosa laxa rootstock. From 2015-2023, the new variety was grown and assessed and reselected for continued evaluation.

The new variety has been found to undergo asexual propagation in Albrighton, England by a number of routes such as vegetative grafting on to Rosa laxa. Asexual propagation techniques in Albrighton, England, such as vegetative grafting, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of shrub rose plant of the present invention possesses the following combination of characteristics:

(a) forms pink-blend which are mid-pink colored blossoms, (b) provides flowers with 120-130 petals, and (c) exhibits a shrub growth habit.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety displays flowers with more petals, which are smaller in size compared to the unnamed seedling female parent (i.e., the seed parent). Additionally, the different unnamed seedling male parent (i.e., the pollen parent) provides flowers which are apricot, orange in color and is an overall larger plant compared to the new variety. Moreover, the new variety can be readily distinguished from non-parental related similar varieties. For example, the 'AUSkitchen' variety (U.S. Plant Pat. No. 23099) produces smaller sized leaves and flowers with fewer petals compared to leaves and flowers produced by the new variety.

The new variety has been named the 'AUSB44A16' variety.

BRIEF DESCRIPTION OF THE PHOTOGRAPHS

The accompanying photographs show, as nearly true as it is reasonably possible to make the same in a color illustration of this character, typical specimen of the new variety. The rose plants of the new variety were approximately seven years of age and photographs were taken Jun. 7, 2024, while growing in a garden in Albrighton, Wolverhampton, United Kingdom.

FIG. 1 — illustrates individual plant parts of the new variety.

Figure 2:
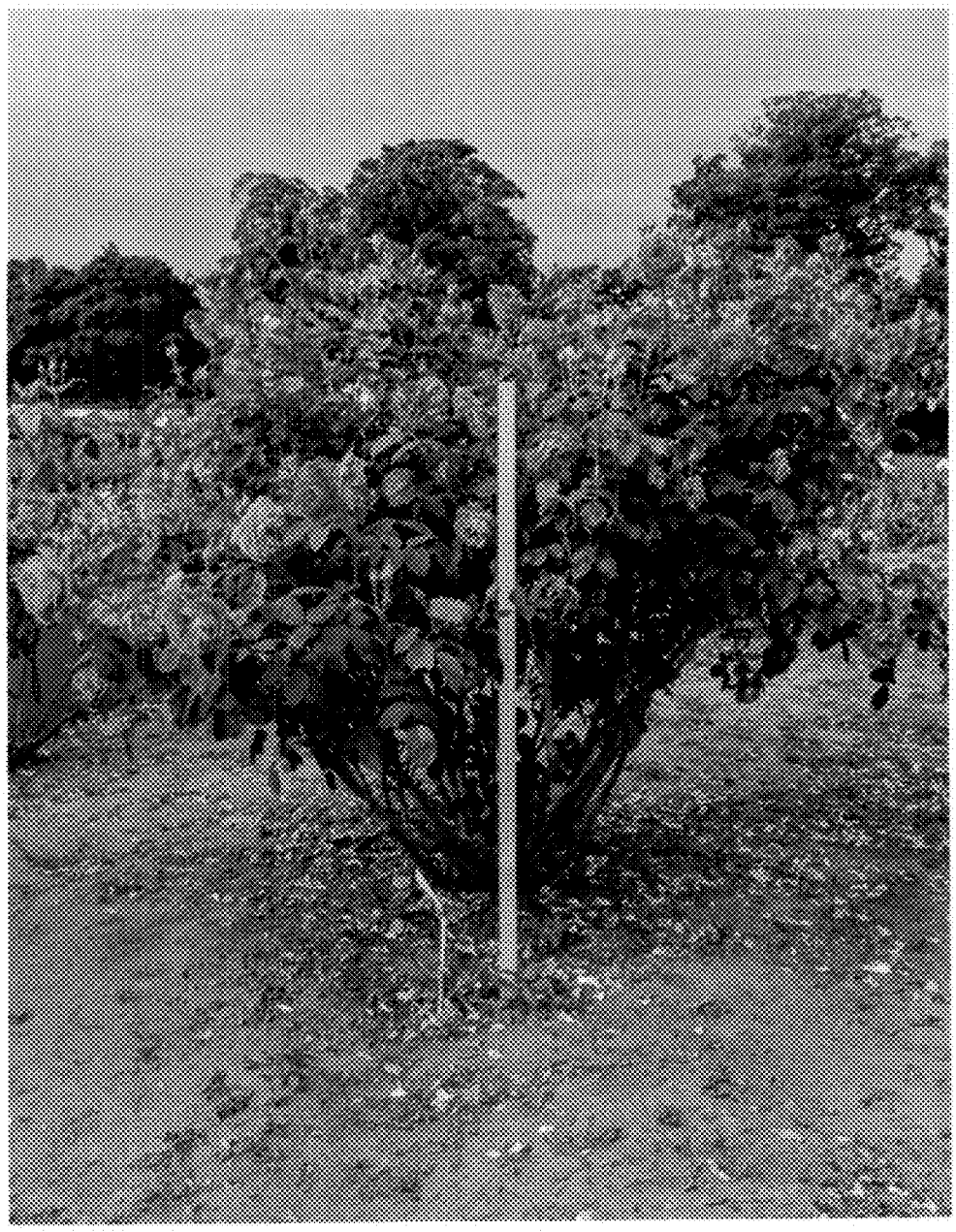

FIG. 2 — illustrates a specimen of the plant displaying flowers at varying points of opening and the overall growth habit.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and the color designation used herein represents the closest color observed on the majority of the specified botanical feature. The description is based on seven-years-old specimens of the new variety, observed during May 2024, while growing in a garden environment at Albrighton, Wolverhampton, United Kingdom.

Botanical classification: *Rosa hybrida* cultivar 'AUSB44A16'.

Commercial classification: Shrub Rose.

Plant:

*Habit*.—Semi-upright.

*Height*.—Approximately 125.0 cm on average.

*Width*.—Approximately 125.0 cm on average.

Branches:

*Stem color*.—Old wood: Yellow-Green Group 146C. — young stems: Yellow-Green Group 146C.

*Length*.—Main stems: approximately 110.0 cm on average. — secondary stems: approximately 70.0 cm on average.

*Diameter*.—Main stems: approximately 1.5 cm on average. — secondary stems: approximately 1.2 cm on average.

*Prickles*.—Young prickles: length was not recorded; width was not recorded; and color is Greyed-Purple Group 187A. — mature prickles: length is approximately 0.6 cm on average; width is approximately 0.5 cm on average at base; and color is Grey-Brown Group N199A.

*Anthocyanin coloration of young shoots*.—Absent to very weak.

*Internode length*.—Approximately 4.7 cm on average.

Leaflets:

*Number*.—Mostly 5, occasionally 7 (including terminal leaflet).

*Shape*.—Pointed oval; apex is acuminate; and base is cordate.

*Margin*.—Serrate.

*Undulation*.—Weak.

*Glossiness of upper side*.—Weak.

*Texture*.—Upper surface: smooth. — under surface: smooth.

*Venation pattern*.—Reticulate.

*Venation color*.—Upper surface color: Yellow-Green Group 147A. — under surface color: Yellow-Green Group 147A.

*Size*.—Terminal leaflet: length is approximately 6.7 cm on average; width is approximately 4.6 cm on average. — lower leaflets: length is approximately 6.2 cm on average; width is approximately 4.0 cm on average. — leaf: length is approximately 15.8 cm on average; width is approximately 11.8 cm on average.

Foliage:

*Young foliage*.—Upper surface color: Yellow-Green Group 146B. — under surface color: Yellow-Green Group 146C in the center with a perimeter of Red-Purple Group 59A.

*Mature foliage*.—Upper surface color: Yellow-Green Group 147A. — under surface color: Yellow-Green Group 147B.

*Petiole* .—Texture: upper surface is glandular; under surface has prickles. — length: approximately 4.7 cm on average. — width: approximately 0.17 cm on average. — upper surface color: Green Group 138B. — under surface color: Green Group 138B.

*Rachis*.—Upper surface color: Green Group 138B. — under surface color: Green Group 138B.

*Stipules*.—Length: approximately 3.0 cm on average. — margin: smooth and glandular. — upper surface color: Yellow-Green Group 144A. — lower surface color: Yellow-Green Group 144A.

Inflorescence:

*Number of flowers*.—Profuse.

*Number of blossoms per stem or in a cluster*.—Typically 8 to 9 blooms per cluster.

*Peduncle*.—Color. Yellow-Green Group 144A. — diameter: approximately 0.27 cm on average. — length: approximately 3.7 cm on average. — surface texture: smooth with prickles.

*Sepals*.—Number: 3 lightly appendaged sepals; 2 unappendaged sepals. — upper surface color and texture: Green Group 143C, smooth and slightly hairy. — under surface color and texture: Yellow-Green Group 144A, smooth and slightly hairy. — size: length is approximately 3.3 cm on average; width is approximately 0.95 cm on average. — margin: smooth and glandular. — extensions: weak-medium. — apex: acuminate.

*Buds*.—Shape: long and broad-based; pointed ovoid. — size: length is approximately 3.0 cm on average; width is approximately 1.9 cm on average. — color (when opening): upper surface is Red Group 39B in the center with Red-Purple Group N57B on the outside; under surface is mostly Red-Purple Group 65C, but some are Red Group 50B and some are a mix of Red-Purple Group 65C and Red Group 50B.

*Flower*.—Form: double. — profile: upper part is flattened convex; lower part is sometimes concave and sometimes flat. — shape when viewed from the top: irregularly rounded. — diameter: approximately 8.0 cm on average. — height: approximately 3.2 cm on average. — duration: on the plant typically 5 to 7 days; not tested as a cut flower. — petal color when opening: upper surface is Red-Purple Group 67B on the outer, blending to Red Group 47D in the middle; lower surface is Red Group 51C; basal spot is medium and Yellow Group 13A. — petal color when fully open: upper surface is Red-Purple Group 67B on the outer, blending to Red Group 47D in the middle; lower surface is Red Group 51C; basal spot is medium and Yellow Group 13A. — petals reflex one by one: medium-strong, outer petals only.

*Fragrance*.—Slight-moderate tea fragrance.

*Petal*.—Number: typically 125 to 126. — drop: petals hang on and dry. — length: approximately 4.3 cm on average. — width: approximately 3.1 cm on average. — overall shape: outer petals are round and inner petals are obovate. — margin: entire. — apex shape: rounded. — base shape: acute.

*Petaloids*.—Number: typically 5 to 6. — length: approximately 2.0 cm on average. — width: approximately 1.0 cm on average. — color: Red Group 39B.

*Stamen*.—Number: mostly none, sometimes 1 to 2. — anthers: color is Yellow Group 13B; length is approximately 0.2 cm on average; and shape is standard. — filaments: length is approximately 0.3 cm on average; width is approximately 0.1 cm on average; and color is Yellow Group 9A.

*Pistils*.—Number: typically 47 to 48. — style: length is approximately 0.75 cm on average; width is approximately 0.1 cm on average; and color is Green-White Group 157A. — stigma: length is approximately 0.1 cm on average; diameter is less than 0.1 cm; shape was not recorded; color is Yellow Group 10A.

*Receptacle*.—Diameter: approximately 0.9 cm on average. — depth: approximately 1.0 cm on average. — shape: pitcher shaped. — color: Yellow-Green Group 144A. — surface texture: smooth.

*Pollen*.—Amount: scarce. — color: unable to ascertain.

*Hips/seed*.—None observed.

Development:

*Vegetation*.—Medium vigor.

*Blossoming*.—Repeat flowering in Albrighton, United Kingdom in flushes from late spring to early winter; blooms may continue year-round if grown inside a warm greenhouse.

*Resistance to diseases*.—Resistance for powdery mildew (*Podosphaera pannosa*), black spot (*Diplocarpon rosae*) and rust (*Phragmidium tuberculatum*) under normal greenhouse growing conditions in Albrighton, United Kingdom.

*Hardiness*.—Not tested.

The new 'AUSB44A16' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of shrub rose plant named 'AUSB44A16', substantially as herein shown and described.

* * * * *